United States Patent [19]

Muchin

[11] Patent Number: 5,161,688
[45] Date of Patent: Nov. 10, 1992

[54] SAMPLER AND METHOD OF MAKING THE SAME

[76] Inventor: Jerome D. Muchin, 320 Comstock Ave., Los Angeles, Calif. 90024

[21] Appl. No.: 405,694

[22] Filed: Sep. 11, 1989

Related U.S. Application Data

[63] Continuation-in-part of Ser. No. 185,208, Apr. 22, 1988, abandoned.

[51] Int. Cl.$^5$ .................. B65D 75/26; A45D 40/00
[52] U.S. Cl. ................. 206/484; 132/320; 206/581; 206/823; 283/56; 53/452
[58] Field of Search ............... 53/452, 453, 456; 132/216, 218, 286, 294, 295, 317, 319, 320, 333; 206/37, 205, 209, 210, 229, 484, 486, 527, 581, 823; 281/15.1; 283/56; 401/88, 96, 97, 126, 129, 132, 262, 264-267

[56] References Cited

U.S. PATENT DOCUMENTS

| | | | |
|---|---|---|---|
| 1,582,242 | 4/1926 | Booty | 206/823 |
| 1,868,399 | 7/1932 | Slezak | 206/229 |
| 2,185,386 | 1/1940 | Valentine | 206/823 |
| 2,561,400 | 7/1951 | Morrell | 206/229 |
| 3,806,260 | 4/1974 | Miller | 401/132 |
| 4,596,481 | 5/1986 | Tanaka | 401/132 |
| 4,687,476 | 8/1987 | Pailin | 206/484 |
| 4,751,934 | 6/1988 | Moir et al. | 132/319 |
| 4,805,773 | 2/1989 | Sabongi | 206/581 |
| 4,824,143 | 4/1989 | Grainger | 132/317 |
| 4,848,378 | 7/1989 | Moir et al. | 132/319 |
| 4,876,136 | 10/1989 | Chang et al. | 132/320 |
| 4,878,775 | 11/1989 | Norbury et al. | 401/132 |
| 4,890,872 | 1/1990 | Parrotta et al. | 132/317 |
| 4,923,063 | 5/1990 | Tarauj | 206/484 |
| 4,925,667 | 5/1990 | Fellows et al. | 132/295 |

FOREIGN PATENT DOCUMENTS

| | | | |
|---|---|---|---|
| 0197184 | 10/1986 | European Pat. Off. | 132/286 |
| 0252001 | 1/1988 | European Pat. Off. | 132/286 |
| 0333604 | 9/1989 | European Pat. Off. | 132/319 |
| 8807825 | 10/1988 | PCT Int'l Appl. | 132/294 |
| 0890517 | 2/1962 | United Kingdom | 401/266 |

*Primary Examiner*—Jimmy G. Foster
*Attorney, Agent, or Firm*—Merchant, Gould, Smith, Edell, Welter & Schmidt

[57] ABSTRACT

A sample of a cosmetic, such as a color, or a fragrance, is enclosed in a retaining cavity contained in a sampler. The sampler includes a base ply with a closure ply affixed to one side to cover a hole punched through the base ply to define the retaining cavity. A film ply is adhesively affixed to the other side of the base ply, also covering the punched hole, to thereby enclose the cosmetic in the retaining cavity. To use the sampler, the film ply is removed exposing the cosmetic.

In a preferred embodiment, the sampler is made by punching a hole through a laminate formed of a base ply lying between a base ply adhesive and backing ply on one side and a liner adhesive and a liner ply on the other. The liner ply is removed and a closure ply affixed to the liner ply adhesive to form a retaining cavity. A cosmetic is then placed in the cavity. The backing ply is then removed, along with any residual cosmetic, and replaced by affixing a film ply to the base ply adhesive.

6 Claims, 3 Drawing Sheets

5,161,688

SAMPLER AND METHOD OF MAKING THE SAME

This application is a continuation-in-part of U.S. patent application Ser. No. 07/185,208, filed Apr. 22, 1988, now abandoned.

BACKGROUND OF THE INVENTION

This invention relates to samplers and, in particular, to cosmetic samplers and methods of making the same.

Important in a consumer's choice of a cosmetic is the opportunity to sample the product personally. As used in the context of the specification and claims, unless otherwise clearly indicated, "cosmetic" includes fragrances, and skin, hair and nail products in their various physical forms.

No matter what recommendations are made by either a sales clerk, or modernly through an interactive computer, as to what colors match what complexion or what fragrance might be most satisfactory, consumers generally prefer to personally see or smell a product applied to themselves before making a purchase. A typical cosmetic counter will include a testing display, which may include lipstick, blushes, or mascara for consumers to test, either for product sampling or to determine their best color. The counter is also likely to include a variety of bottles, jars or atomizers filled with fragrances or skin care products Unfortunately, many consumers have become wary of such displays fearing who might previously have used or had access to the samples. For example, a consumer may be afraid of catching a contagious disease from a previous user of a lipstick or an eye shadow or afraid that a bottle of perfume or jar of skin care cream has been adulterated.

Several attempts have been make to overcome the concerns caused by multiple use samples, by providing individual samples. For example, cosmetic companies have given away small bottles of products and provided products on paper tabs as rub-off testers for powder make-up and lipstick. These methods, however, suffer from various drawbacks. They may be too costly, provide too little sample or they may affect the product, so that what is applied is not the same as the actual product.

Additional problems arise when samples, such as perfumes or fragranced creams and lotions, are included in magazines or direct mail items. Those responsible for handling the magazines and direct mail items, or those who receive the material, but are not interested in a particular product, may find the scent which leaks from conventional samples offensive. In some cases, there may even be an allergic reaction to the samples.

Now, in accordance with this invention, there is provided a convenient, hygienically-safe, individual sampler which overcomes these drawbacks. The amount provided by the sampler is enough for a full presentation of color or fragrance; there can be enough product for application to cheeks, eyes, lips and the like. The potential customer can apply the sample safely and conveniently anywhere — at a department store counter, at home or at the office — and know that the sample of color or fragrance will be identical to the actual product. Further, the sample is virtually leak-free thus minimizing any problems of imparting an undesired odor to a magazine or direct mail item or causing allergic reactions, because the sample is not exposed until a potential customer wishes. There is also provided a method for manufacturing such samplers.

SUMMARY OF THE INVENTION

The sampler of this invention includes a base ply having a first surface and a second surface opposite the first surface with a hole therethrough and having a closure ply affixed to the first surface, so as to cover the hole and define a retaining cavity in the base ply. A cosmetic, such as a color or fragrance is placed in the retaining cavity and a film ply affixed to the second surface of the base ply to cover the hole and enclose the cosmetic. The film ply is removable to expose the cosmetic, so that it may be sampled at the convenience of a potential customer.

In one embodiment, an adhesive is provided on the exterior surface of either the film ply or the closure ply, so that the sampler can be adhesively affixed to a carrier, such as the packaged product, magazine page, coupon, direct mailer, point of purchase display or the like.

In one embodiment, the sampler is made by forming a hole through a laminate having a base ply sandwiched between a base ply adhesive and backing ply on one side and a liner adhesive and liner ply on the other. Once the hole is formed the liner ply is removed and a closure ply is affixed, thereby forming a retaining cavity. A cosmetic is then placed in the cavity and the backing ply, along with any residual cosmetic, is then removed. Finally, a removable film ply is affixed to enclose the cosmetic in the cavity.

BRIEF DESCRIPTION OF THE DRAWINGS

A complete understanding of the invention and of the above and other advantages and features thereof may be gained from consideration of the following description of the preferred embodiments taken in conjunction with the accompanying drawings in which.

DETAILED DESCRIPTION

Figure 1:
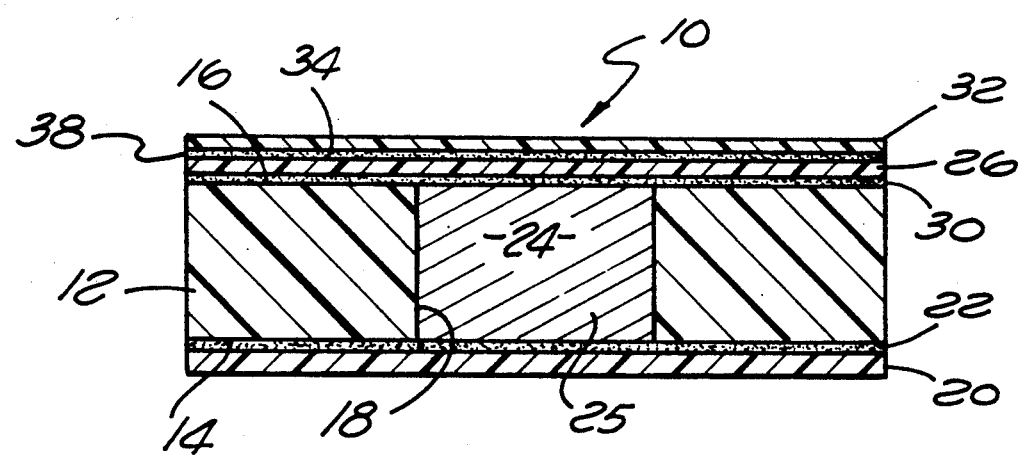
FIG. 1 is a cross-sectional view of a cosmetic sampler in accordance with the invention.
Figure 2:
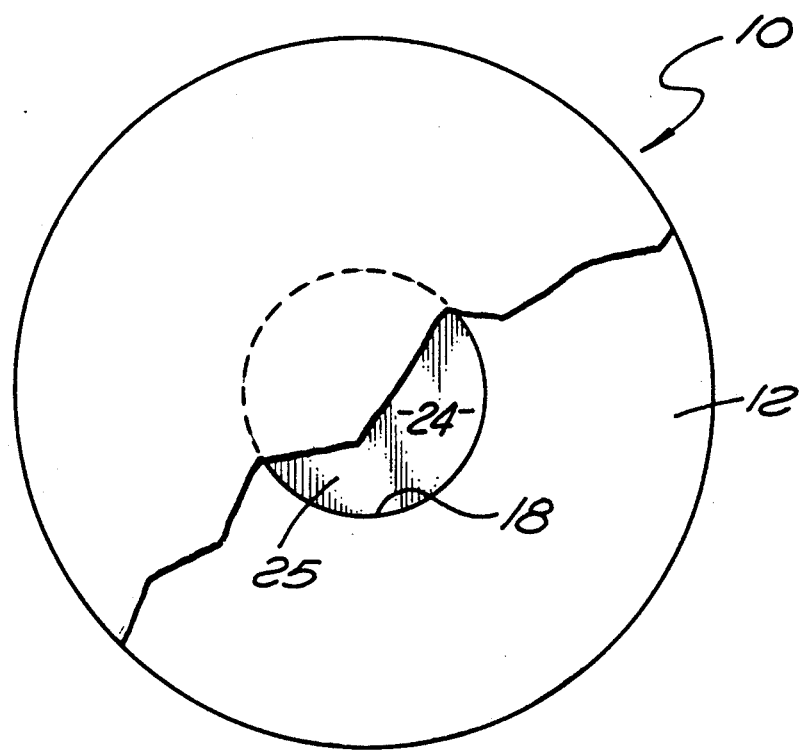
FIG. 2 is a top view, partially broken away, of the cosmetic sampler of FIG. 1.

Referring to FIGS. 1 and 2, a cosmetic sampler 10 in accordance with the invention includes a base ply 12, with a first surface 14 on one side, a second surface 16 on the other side, opposite the first surface 14, and a hole 18 punched through the base ply 12. In one embodiment, the base ply 12 is a plastic foam having a thickness from about 1/32" to about 1/16" thereby being inherently flexible with the hole 18 being circular with a diameter of approximately ⅜". Of course, other dimensions and configurations are also possible, depending on the amount of the sample and the manner in which the sample is to be removed from the cavity. Alternatively, the base ply may be of a material which is embossed, punched or otherwise configured to form a cavity therein, without the need to make a hole therethrough.

In those embodiments having a hole punched therethrough, a closure ply 20, which may be a clear plastic ply, such as Mylar or other similar plastic material, is affixed to the first surface 14 with a closure ply adhesive 22, so as to cover one end of the hole 18. A cosmetic retaining cavity 24 is thereby defined by the sides of the hole 18 through the base ply 12 and the portion of the closure ply 20 extending across the hole opening at the first surface 14. If the cavity is formed in a single layer by embossing or the like, then no closure ply 20 or closure ply adhesive 22 will be necessary.

A cosmetic 25, such as a color or fragrance is placed in the cosmetic retaining cavity 24. The cosmetic can be in various physical forms such as liquid, including creams and lotions as well as powders. Representative formulations that may be enclosed in the retaining cavity include:

FRAGRANCE POMADE

| | % |
|---|---|
| Petrolatum | 10.0 |
| Microcrystalline Wax | 15.0 |
| Ozokerite | 5.0 |
| Silica | 2.0 |
| Fragrance Oil | 20.0 |
| Mineral Oil | 48.0 |

Melt all ingredients except the fragrance oil together and keep stirring. Start to cool and add the fragrance oil at 50° C.

FRAGRANCE CREAM SACHET

| | % |
|---|---|
| Water | 80.15 |
| Triethanolamine | 0.7 |
| Methyl paraben | 0.1 |
| Polysorbate 20 | 0.15 |
| Carbomer 940 | 0.3 |
| PPG-30 Cethyl Ether | 4.0 |
| Stearic Acid | 7.5 |
| Propylparaben | 0.1 |
| Fragrance | 7.0 |

Disperse the Carbomer in the water and add the methylparaben, polysorbate 20 and heat to 80° C. and add the triethanolamine. In a separate jacketed tank add the PPG-30 Cetyl Ether, stearic acid and propylparaben and heat to 80° C. with constant stirring. Add the oil phase to the water phase with high speed mixing and emulsify. Cool to 50° C. and add the fragrance oil.

BLUSHER GELEE

| | % |
|---|---|
| Alcohol | 45.0 |
| Carbomer 940 | 1.4 |
| Lauryl Lactate | 1.5 |
| Diisopropyl adipate | 1.5 |
| PEG-4 | 3.0 |
| F.D.C. Red 40 | 0.05 |
| Linoleamide DEA | 3.5 |
| Quaternium 15 | 0.1 |
| Water, D.I. | 43.75 |
| Triethanolamine | 0.2 |

Predisperse the Carbomer in water and alcohol and add the lauryl lactate, diisopropyl adipate, PEG-4 and Red 40. Add Quaternium 15 until homogeneous. Reserve about 5% of the water to mix with the linoleamide DEA and triethanolamine before adding to the batch.

LIPSTICK

| | % |
|---|---|
| Carnauba Wax | 3.0 |
| Candelilla Wax | 7.0 |
| Ozokerite | 2.0 |
| Microcrystalline Wax | 1.0 |
| Beeswax | 6.0 |
| Lanolin | 10.0 |
| Castor Oil | 60.0 |
| Lake Colors | 10.6 |

-continued
LIPSTICK

| | % |
|---|---|
| Propylparaben | 0.2 |
| Fragrance | 0.2 |

Melt the waxes together and add the lanolin and castor oil with constant mixing. The lake colors should be roller milled with an equal amount of castor oil and added to the batch. Propylparaben can be added when the temperature reaches 70° C. Cool to 60–70° C. and add the fragrance.

CONCEALER

| | % |
|---|---|
| Castor Oil | 30.0 |
| Petrolatum | 5.5 |
| Butyl Stearate | 10.0 |
| Beeswax | 10.0 |
| Microcrystalline Wax | 8.0 |
| Butylparaben | 0.1 |
| Isopropyl Myristate | 8.3 |
| Titanium Dioxide | 23.0 |
| Pigments-iron oxides | 5.0 |
| Fragrance | 0.1 |

Melt the oils and waxes until homogeneous. Add the powders and put the mixture through a suitable mill, until the shade develops. Reheat to displace air entrapment and add the fragrance with constant slow stirring.

POWDER EYESHADOW

| | % |
|---|---|
| Talc | 58.68 |
| Kaolin | 16.0 |
| Zinc Stearate | 10.0 |
| Isopropyl Palmitate | 4.0 |
| BHA | 0.02 |
| Titanium dioxide | 1.3 |
| Pigments and Pearl | 10.0 |

Mix and micropulverize the powders and pigments. Spray in the Isopropyl Palmitate and mix with pearl until homogeneous.

ZINC OXIDE OINTMENT

| | % |
|---|---|
| Zinc Oxide powder | 20.0 |
| Lanolin | 7.0 |
| Tocopherol Acetate | 1.0 |
| Petrolatum, white | 72.0 |

Mill the zinc oxide with the lanolin until smooth. Add the petrolatum and tocopherol acetate with constant mixing until homogeneous. A little heat can be used to facilitate mixing.

In some embodiments, particularly where the cosmetic is a volatile liquid or only a small amount is desired, the sample is first absorbed onto an absorbent material (not shown), such as a die cut sponge, paper, cloth or molecular sieve and the absorbent material then placed into the retaining cavity. Once the sample is exposed, there is a controlled transpiration of the absorbed fragrance, skin oil, etc. Such embodiments can also include a perforated ply over the opening of the retaining cavity to allow exposure or evaporation of the sample without direct contact of the sample with other surfaces. The amount of exposure or rate of evaporation can be regulated by the size and number of perforations.

A film ply 26, which can be-a plastic film, such as a polyester film, is affixed to the second surface 16 of the base ply 12, so as to extend across the opening of the hole 18 at the second surface 16, thereby closing the retaining cavity 24 and enclosing the cosmetic 25 in the retaining cavity 24. The film ply 26 is removably affixed to the second surface 16 by any suitable means, such as using a base ply adhesive 30. In some embodiments, the base ply adhesive is chosen so that sufficient adhesive remains after the film ply has been removed to enable the samples to adhere to a surface, such as the skin of the user. Thus, the sampler may be used to directly contact the sample to the surface.

In some embodiments, a carrier ply 32 is removably affixed to a surface 34 of film ply 26, opposite the surface of the film ply 26, adjacent the second surface 16 of the base ply 12. An application adhesive 38 is disposed between the carrier ply 32 and the film ply surface 34 of the film ply 26 to provide a means for affixing the sampler to a carrier, such as the packaged product, magazine page, coupon, direct mailer, point of purchase display or the like. In such an embodiment, when the carrier ply 32 is removed, the application adhesive 38 is used to affix the cosmetic sampler to a carrier. When the sampler is ultimately removed, the film ply 26 will remain affixed to the carrier and the rest of the sampler will pull free.

In other embodiments (not shown), the carrier ply is removably affixed to the surface of the closure ply opposite the surface of the closure ply adjacent the first surface of the base ply. The application adhesive is disposed between the carrier ply and the closure ply to provide a means of affixing the sampler to the carrier. In these embodiments, when the sampler is ultimately removed, it is the film ply which is pulled free, while the rest of the sampler remains affixed to the carrier.

Referring to FIGS. 3a, 3b, 3c, 3d, 3e and 3f, a preferred method of making a sampler in accordance with the invention is illustrated. Initially, a laminate sheet 50 is formed which includes a base ply 52, having applied on one side a base ply adhesive 54 and then a backing ply 56 covering the base ply adhesive 54 and on the opposite side having applied a liner adhesive 66 and then a liner ply 68 covering the liner ply adhesive. The backing ply 56 is preferably a non-porous, non-resilient backing with a smooth surface, most preferably the backing is a plastic film, such polypropylene film.

Figure 3A:
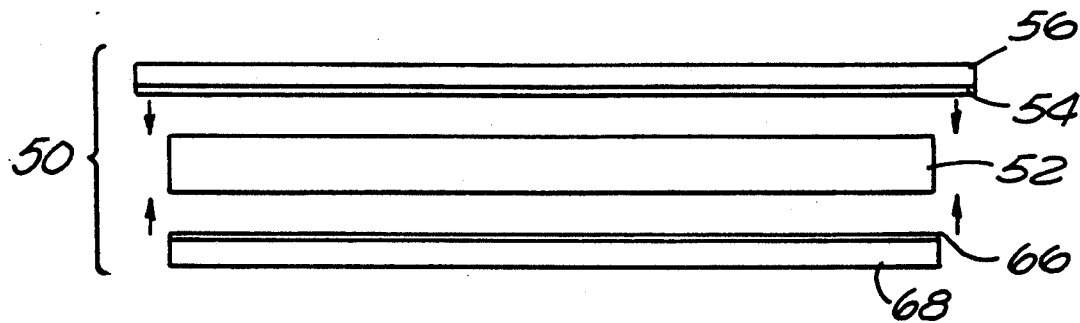
FIGS. 3a, 3b, 3c, 3d, 3e and 3f are cross-sectional views of cosmetic samplers at various stages of manufacture, illustrating preferred methods of making cosmetic samplers in accordance with the invention.
Figure 3B:
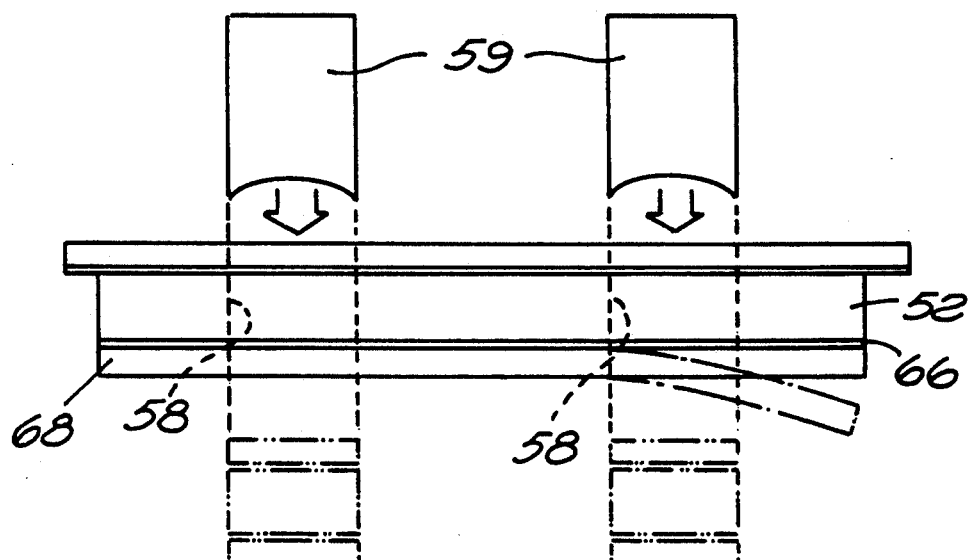

Referring to FIG. 3b, holes such as holes 58 are punched through the laminate sheet using a suitable punch 59 or other die cutting tool well known in the art. The liner ply 68 is then removed and discarded, leaving the liner adhesive 66 on the surface of the base ply 52.

Figure 3C:
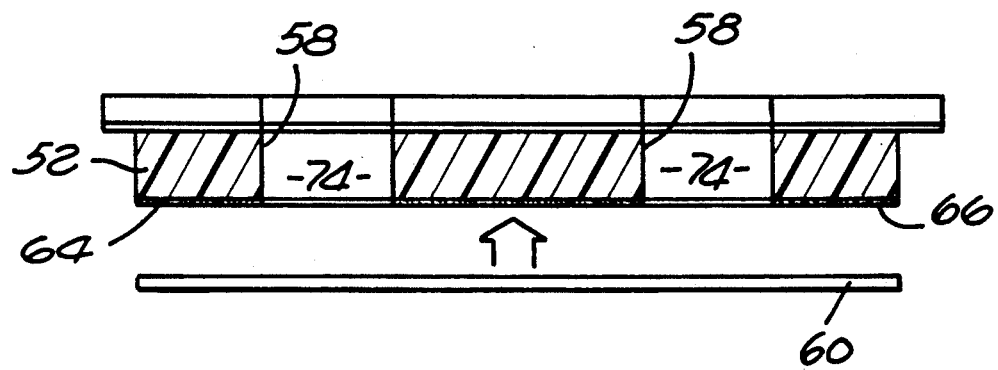
Figure 3D:
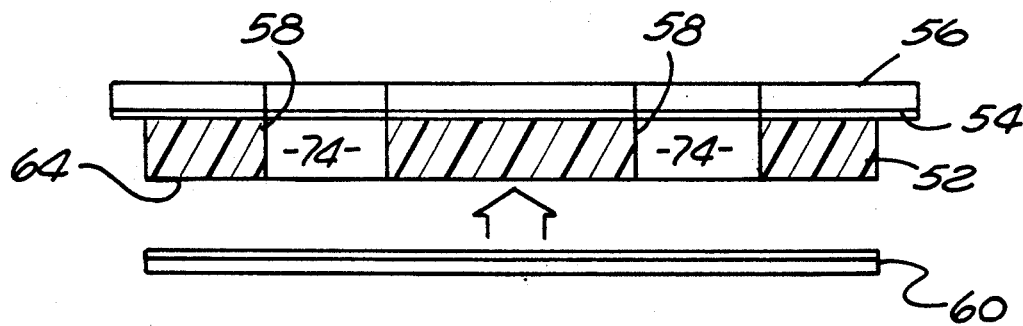

Referring to FIG. 3c, once the holes 58 have been punched through the laminate and the liner ply 68 removed to expose the liner adhesive 66, a closure ply 60 is affixed over a first surface 64 of the base ply 52, so as to cover the holes 58 thereby creating a plurality of retaining cavities 74. This embodiment results in no adhesive on the portion of the closure ply 60 which covers the holes 58.

In another embodiment, shown in 3d, the laminate is comprised of only the base ply 52, the base ply adhesive 54 and the backing ply 56. After the holes 58 are punched, a closure ply 60 is then applied to the first surface 64 of the base ply 52, to form a plurality of retaining cavities 74. This embodiment results in an adhesive on the portion of the closure ply 60 which covers the holes 58. In lieu of the punching step and the application of the closure ply, the laminate sheet can be made of an embossable material which is embossed to form the retaining cavity.

Figure 3E:
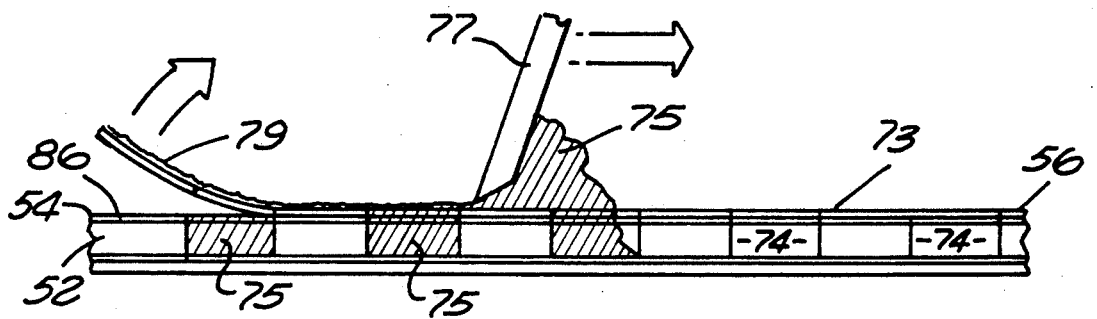

Referring to FIG. 3e, a cosmetic 75 is placed on the top surface 73 of the backing ply 56 of the laminate sheet and a knife edge or squeegee-like tool 77 used to scrape or squeegee the cosmetic 75 across the top surface 73 causing the cosmetic 75 to be deposited in the retaining cavities 74. Of course, other means for depositing the cosmetic 75 in each of the cavities 74 may be used without departing from the invention. The cosmetic deposited in the cavities can be a clear liquid or an emulsion with pre-defined viscosity. However, the use of non-liquids, such as powders, creams, gels and the like may also be used without departing from the spirit of the invention. As will be readily appreciated by one skilled in the art, the sampler need not be limited to cosmetic samples but can be filled with other products, such as suntan lotion and topical substances including benzoyl peroxide cream.

Once the cosmetic has been deposited in each of the cavities 74, the backing ply 56, along with any residue 79 on the backing ply surface 73, is peeled from the second surface 86 of the base ply 52, thereby exposing the base ply adhesive 54. Thus, the backing ply 56 acts as a mask or protector for the base ply adhesive 54 to prevent the cosmetic 75 from coming in contact with the base ply adhesive 54 when the cosmetic 75 is being squeegeed across the top surface 73 to deposit the cosmetic in the cavities 74.

Figure 3F:
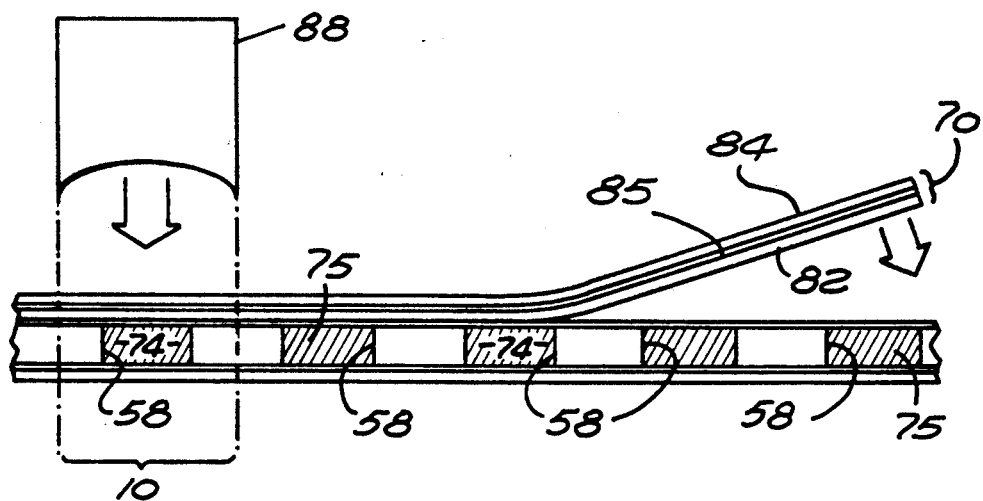

Referring to FIG. 3f, a film laminate 70, which includes a film ply 82, a carrier ply 84 and an application adhesive 85, between the carrier ply 84 and the film ply 82, is applied over the top surface 73 covering the various holes 58 thereby enclosing the cosmetic 75 in each of the cavities 74. With some cosmetics, such as with lipsticks, it is often desirable to briefly pass the cosmetic-film ply interface over a flame. The flame treatment enhances the appearance of the surface, such as by imparting an aesthetically pleasing gloss. A cutting tool 88 is then used to cut at least one individual sampler, such as the sampler 10.

Referring to FIG. 1, to affix the cosmetic sampler to a carrier, the carrier ply 32 is removed from the applicator 10 to expose the application adhesive 38. The remaining cosmetic sampler is affixed to the carrier.

Various other modifications and variations of the present invention are possible without departing from the spirit of the invention. For example, the various adhesives used to affix layers together may be transfer adhesives or may be applied in a patterned manner to one layer. Alternatively, other means such as heat fusing and the like may be used to join various layers.

The method in accordance with the invention results in samples having no torn edges, holes or blisters and the sample is free of embedded particles, foreign matter or surface dirt. A further advantage is that there is no odor "leak" from samplers containing a fragrance. This means that the samples can be affixed to magazine pages and the like without imparting any smell, until the sampler is opened by the user.

What is claimed is:
1. A sample holder comprising:
 a planar, flexible base ply having a hole therethrough;
 a planar, flexible closure ply affixed to the base ply, the hole and the closure ply thereby defining a retaining cavity for the sample;
 a planar, leak-proof, flexible film ply removably affixed to the base ply covering the hole and enclosing the sample in the retaining cavity between the planar, flexible closure ply and the planar, leak-proof, flexible film ply; and
 a uniform layer of base ply adhesive between the planar, leak-proof, flexible film ply and the planar, flexible base ply affixing the planar, leak-proof, flexible film ply to the planar, flexible, base ply.

2. A method of a making a sampler comprising the steps of:

punching at least one hole through a laminate sheet, the laminate sheet comprising a base ply, a base ply adhesive on a first side of the base ply and a backing ply covering the base ply adhesive;

affixing a closure ply to a second side of the foam ply, opposite the first side, for covering the punched hole through the laminate sheet and a defining retaining cavity in the laminate sheet;

depositing a sample in the retaining cavity;

removing the backing ply from the base ply to expose the base ply adhesive on the first side of the base ply;

affixing a film ply to the first side of the foam ply to cover and enclose the retaining cavity.

3. The method of claim 2 further comprising applying an application adhesive on one side of the film ply opposite the first side of the base ply, and then affixing a carrier ply over the application adhesive, the carrier ply being removable to expose the application adhesive when the substance applicator is to be affixed to a carrier.

4. The method of claim 2 further comprising applying an application adhesive on one side of the closure ply opposite the second side of the base ply, and then affixing a carrier ply over the application adhesive, the carrier ply being removable to expose the application adhesive when the sampler is to be affixed to a carrier.

5. The method of claim 2 further comprising cutting at least one individual region from the composite laminate, each having at least one retaining cavity with the sample contained therein.

6. A method of making a sampler comprising the steps of:

punching at least one hole through a laminate sheet, the laminate sheet comprising a base ply, a base ply adhesive on a first side of the base ply and a backing ply covering the base ply adhesive and a liner ply adhesive on the second side of the base ply and a liner ply covering the base ply adhesive:

removing the liner ply and affixing a closure ply to the liner ply adhesive for covering the punched hole through the laminate sheet and defining a retaining cavity in the laminate sheet;

depositing a sample in the retaining cavity;

removing the backing ply from the base ply to expose the base ply adhesive on the first side of the base ply;

affixing a film ply to the first side of the base ply to cover and enclose the retaining cavity.

* * * * *